United States Patent [19]

Lewis

[11] Patent Number: 4,849,575
[45] Date of Patent: Jul. 18, 1989

[54] PRODUCTION OF OLEFINS

[75] Inventor: Jeffrey M. O. Lewis, Charleston, W. Va.

[73] Assignee: UOP, Des Plaines, Ill.

[21] Appl. No.: 125,226

[22] Filed: Nov. 25, 1987

[51] Int. Cl.$^4$ .............................................. C07C 1/00
[52] U.S. Cl. .................................................... 585/640
[58] Field of Search ........................................ 585/640

[56] References Cited

U.S. PATENT DOCUMENTS

| | | | |
|---|---|---|---|
| 4,079,095 | 3/1978 | Givens et al. | 260/682 |
| 4,238,631 | 12/1980 | Daviduk et al. | 585/469 |
| 4,328,384 | 5/1982 | Daviduk et al. | 585/469 |
| 4,423,274 | 12/1983 | Daviduk et al. | 585/640 |
| 4,499,327 | 2/1985 | Kaiser | 585/640 |
| 4,520,216 | 5/1985 | Skov et al. | 585/640 |
| 4,556,645 | 12/1985 | Coughlin et al. | 502/66 |
| 4,579,830 | 4/1986 | Coughlin | 502/66 |
| 4,686,313 | 8/1987 | Bell et al. | 585/640 |

OTHER PUBLICATIONS

Chang, Clarence D., Hydrocarbons from Methanol, Marcel Dekker, Inc., New York (1983), pp. 21–26.

Primary Examiner—Curtis R. Davis
Attorney, Agent, or Firm—Thomas K. McBride; John G. Tolomei; Warren K. Volles

[57] ABSTRACT

A process for producing olefins comprising:
(a) contacting hydrogen and at least one carbon oxide in a first reaction zone at conditions effective to chemically react the hydrogen and carbon oxide and produce at least one product, e.g., methanol, in the effluent of the first reaction zone;
(b) contacting the effluent containing the product in a second reaction zone at conditions effective to chemically react the product and produce olefins in the effluent of the second reaction zone;
(c) recovering an olefin-enriched product from the effluent of the second reaction zone; and
(d) subjecting at least one of hydrogen and at least one carbon oxide from the effluent of the second reaction zone to step (a).

35 Claims, 2 Drawing Sheets

PRODUCTION OF OLEFINS

FIELD OF THE INVENTION

This invention relates to a process for producing one or more olefins. More particularly, the invention relates to an integrated process for producing such olefins which involves hydrogen and at least one carbon oxide, i.e., the carbon monoxide and/or carbon dioxide, as feedstock.

The following Table shows the status of all applications referred to in this specification:

| Serial Number | Filing Date | Status |
| --- | --- | --- |
| 599,771 | April 13, 1984 | Abandoned |
| 599,776 | " | Abandoned |
| 599,807 | " | Abandoned |
| 599,809 | " | Abandoned |
| 599,811 | " | Abandoned |
| 599,812 | " | Abandoned |
| 599,813 | " | Abandoned |
| 600,166 | " | Abandoned |
| 600,168 | " | Abandoned |
| 600,170 | " | pending |
| 600,171 | " | 4,686,093 |
| 600,173 | " | 4,683,217 |
| 600,174 | " | 4,744,970 |
| 600,175 | " | 4,686,092 |
| 600,179 | " | 4,684,617 |
| 600,180 | " | 4,768,418 |
| 600,181 | " | 4,741,892 |
| 600,182 | " | Abandoned |
| 600,183 | " | Pending |
| 600,312 | " | 4,793,984 |
| 070,574 | July 7,1987 | Pending |
| 070,575 | " | Pending |
| 070,578 | " | Pending |
| 070,579 | " | Pending |

BACKGROUND OF THE INVENTION

Methanol is readily producible from coal and other raw materials by the use of well-known commercial processes. For example, synthesis gas, i.e., a gaseous mixture comprising hydrogen and at least one carbon oxide, in particular carbon monoxide, can be obtained by the partial combustion or gasification of any organic material such as coal, other hydrocarbons, carbohydrates and the like. Synthesis gas can be manufactured into methanol by a well known heterogeneous catalytic reaction using catalysts such as copper-zinc oxide and other copper-based catalysts.

Methanol is frequently used as a feedstock to produce other compounds. For example, "Hydrocarbons from Methanol" by Clarence D. Chang, published by Marcel Dekker, Inc. N.Y. (1983) presents a survey and summary of the technology described by its title. Chang discusses methanol to olefin conversion in the presence of molecular sieves at pages 21-26. Olefin production from methanol has been the subject of a number of patents. For example, see U.S. Pat. Nos. 4,079,095; 4,238,631; 4,328,384; 4,423,274; and 4,499,327. Methanol to olefin conversion is also discussed in commonly assigned U.S. patent applications Ser. Nos. 070,579, 070,574, 070,575 and 070,578, each filed July 7, 1987. Each of the patents and patent applications identified above are incorporated in its entirety by reference herein.

While olefins, in particular light olefins, are often quite valuable, continuing efforts are needed to reduce the cost of production. Recently, these efforts have centered around increasing the selectivity of various catalysts toward converting methanol into the desired olefins. Various processing and catalyst modifications have been suggested, e.g., see the above-noted patents and publication.

However, even though improved selectivities have been achieved, a certain amount of undesired products, e.g., paraffins, heavier olefins and the like, is produced. These undesired products are often discarded or used in applications of reduced value, thereby increasing the feedstock cost per unit of olefins produced.

In addition, conventional processes to produce synthesis gas methanol from synthesis gas and olefins from methanol each involve separate separation steps, e.g., in order to provide pure or specification grade product. These separation steps are relatively capital and labor intensive, and add substantially to the manufacturing costs involved in producing such products. Clearly it would be advantageous to provide a process useful to effectively and economically produce olefins.

SUMMARY OF THE INVENTION

A new process for producing olefins has been discovered. This integrated process effectively combines synthesis gas (or syn gas) processing and olefin production, and involves recycling one or more components. In one broad aspect, the process comprises: (a) contacting hydrogen, and at least one carbon oxide, i.e., the carbon monoxide and/or carbon dioxide, in a first reaction zone at conditions effective to chemically react the hydrogen and carbon oxide, and to produce at least one product, preferably methanol, in the first reaction zone effluent; (b) contacting this effluent, preferably substantially all of this effluent, in a second reaction zone at conditions effective to chemically react the product, and to produce olefins in the second reaction zone effluent; (c) recovering an olefin-enriched product from the second effluent; and (d) subjecting hydrogen and/or at least one carbon oxide from the second effluent to step (a).

In another broad aspect, the present olefins production process comprises (1) contacting hydrogen and at least one carbon oxide in a reaction zone at conditions effective to produce olefins in the effluent of this zone; (2) recovering an olefin-enriched product from the effluent; and (3) subjecting at least one of hydrogen and at least one carbon oxide from the effluent to step (1). In this embodiment, step (1) preferably takes place in the presence of a physical admixture of two or more solid catalysts and/or a single solid catalyst having multiple functionalities, i.e., the ability to promote two or more chemical reactions in the reaction zone.

DISCUSSION OF THE INVENTION

The present olefins producing process provides substantial advantages. For example, the process is integrated in such a manner to achieve substantial economies, e.g., in reduced capital, labor and feedstock costs, and is easily operated and controlled to obtain high ultimate yields of the desired, valuable olefins. In certain embodiments, the need for intermediate separations is reduced or even eliminated. This adds further to the overall effectiveness of the process, and may actualluy benefit one or more of the chemical reactions involved.

Conventional methanol production catalysts, e.g., one or more solid catalysts such as copper-zinc oxide catalysts and, in particular copper-based catalysts useful for low pressure, e.g., about 50 to about 100 atmospheres pressure, methanol production can be employed in step (a). Methanol need not be produced exclusively, but step (a) may produce this alcohol in combination with other products, such as methyl acetate, ethanol, ethyl acetate, mixtures thereof and the like, which react to form olefins in step (b). Although methanol is preferred, the effluent from the first reaction zone need not contain any methanol and such embodiments are included within the scope of the present invention. If such other product or products are desired, the catalyst used in step (a) and the step (a) conditions may be adjusted or controlled within conventional ranges to obtain the desired product mix. Step (a), e.g., the production of methanol from a mixture of hydrogen and carbon oxide, e.g., synthesis gas, is well known.

Since step (a) can be conducted in a conventional and well known manner, a detailed discussion of this step, the conditions at which this step is run and the catalysts suitable for use in this step, need not be presented here. Step (a) should be conducted so as to have no substantial or undue detrimental effect on the present process or the products of the present process.

The hydrogen/carbon oxide reaction or conversion is equilibrium controlled so that the effluent from the first or step (a) reaction zone or zones include not only the desired product, e.g., methanol, but also hydrogen and at least one carbon oxide, as well as other components such as water, methane, and the like. In conventional methanol production, the methanol is separated from these materials. However, in the present process it is preferred that substantially no such separation occurs. In other words, it is preferred that substantially the entire effluent from the first or step (a) reaction zone be sent to step (b). In this embodiment, substantially no separation equipment is required between steps (a) and (b) and substantially all of the product-containing effluent is subjected to step (b).

Step (b) of the present invention involves converting the product or products e.g., methanol, in the effluent from the first or step (a) reaction zone into olefins to produce an olefin-containing effluent from the second or step (b) reaction zone. Step (b) preferably takes place in the presence of a solid catalyst capable of acting to promote the conversion of such product or products to olefins.

The composition of the presently useful product conversion catalyst may vary widely, provided that such catalyst functions to promote the desired conversion at the conditions of step (b). Thus, the catalyst suitable for use in step (b) of the present invention includes at least one of the naturally occurring or synthetic materials capable of promoting the desired product conversion or reaction at the conditions of step (b).

One particularly useful class of methanol conversion catalysts are crystalline microporous three dimensional solid catalysts or CMSCs, i.e., catalysts which promote chemical reactions of molecules having selected sizes, shapes or transition stages. That is, CMSCs are catalysts which promote chemical reactions or feedstock molecules which conform to a given molecular size, molecular shape or transition stage constraint. Different CMSCs have different size/shape/transition stage constraints depending on the physical structure and chemical composition, for example, the effective diameter of the pores, of the catalyst. Thus, the particular CMSC chosen for use depends on the particular feedstock employed, and the particular chemical (reaction) and product desired. Preferably, the CMSC has a substantially uniform pore structure, e.g., substantially uniformly sized and shaped pores. CMSCs include, for example, layered clays; zeolitic molecular sieves and non-zeolitic molecular sieves or NZMSs.

The presently useful NZMSs include molecular sieves embraced by an empirical chemical composition, on an anhydrous basis, expressed by the formula:

$$mR: (Q_w Al_x P_y Si_z)O_2 \qquad (I)$$

where "Q" represents at least one element present as a framework oxide unit "$QQ_2{}^n$" with charge "n" where "n" may be $-3, -2, -1, 0,$ or $+1$; "R" represents at least one organic templating agent present on the intracrystalline pore system; "m" represents the molar amount of "R" present per mole of $(Q_w Al_x P_y Si_z)O_2$ and has a value from zero to about 0.3; and "w", "x", "y" and "z" represent the mole fractions of $QO_2{}^n$, $AlO_2{}^-$; $PO_2{}^+$, $SiO_2$, respectively, present as framework oxide units. "Q" is characterized as an element having a mean "T—O" distance in tetrahedral oxide structures between about 1.51 Å and about 2.06 Å. "Q" has a cation electronegativity between about 125 kcal/g-atom to about 310 kcal/gm-atom and "Q" is capable of forming stable Q—O—P, Q—O—Al or Q—O—Q bonds in crystalline three dimensional oxide structures having a "Q—O" bond dissociation energy greater than about 59 kcal/g-atom at 298° K.[1]; and "w", "x", "y" and "z" represent the mole fractions of "Q", aluminum, phosphorus and silicon, respectively, present as framework oxides said mole fractions being within the limiting compositional values or points as follows:

w is equal to 0 to 99 mole percent;
y is equal to 1 to 99 mole percent;
x is equal to 1 to 99 mole percent; and
z is equal to 0 to 99 mole percent.

[1] See the dicussion at pages 8a, 8b and 8c of EPC Publication 0 159 624, published Oct. 30, 1985, about the characterization of "EL" and "M". Such are equivalent to Q as used herein.

The "Q" of the "QAPSO" molecular sieves of formula (I) may be defined as representing at least one element capable of forming a framework tetrahedral oxide and may be one of the elements arsenic, beryllium, boron, chromium, cobalt, gallium, germanium, iron, lithium, magnesium, manganese, titanium, vanadium and zinc. Combinations of the elements are contemplated as representing Q, and to the extent such combinations are present in the structure of a QAPSO they may be present in molar fractions of the Q component in the range of 1 to 99 percent thereof. It should be noted that formula (I) contemplates the non-existence of Q and Si. In such case, the operative structure is that of aluminophosphate or $AlPO_4$. Where z has a positive value, then the operative structure is that of silicoaluminophosphate or SAPO. Thus, the term QAPSO does not perforce represent that the elements Q and S (actually Si) are present. When Q is a multiplicity of elements, then to the extent the elements present are as herein contemplated, the operative structure is that of the ELAPSO's or ELAPO's or MeAPO's or MeAPSO's, as herein discussed. However, in the contemplation that molecular sieves of the QAPSO variety will be invented in which Q will be another element or elements, then it is the intention to embrace the same as a suitable molecular sieve for the practice of this invention.

Illustrations of QAPSO compositions and structures are the various compositions and structures described in the patents and patent applications set forth in Table A, which follows, and by Flanigen et al., in the paper entitled, "Aluminophosphate Molecular Sieves and the Periodic Table," published in the "New Developments and Zeolite Science Technology" Proceedings of the 7th International Zeolite Conference, edited by Y. Murakami, A. Sijima and J. W. Ward, pages 103–112 (1986):

TABLE A

| Patent or Pat. Applic. No. | Subject Matter of Patent or Patent Application |
|---|---|
| U.S. Pat. No. 4,567,029 | MAPO's are crystalline metal aluminophosphates having a three-dimensional microporous framework structure of $MO_2^{-2}$, $AlO_2^-$ and $PO_2^+$ tetrahedral units and having an empirical chemical composition on an anhydrous basis expressed by the formula $mR:(M_xAl_yP_z)O_2$; where $\underline{R}$ represents at least one organic templating agent present in the intracrystalline pore system; $\underline{m}$ has a typical value of from 0 to 0.3 and represents the moles of $\underline{R}$ present per mole of $(M_xAl_yP_z)O_2$; $\underline{M}$ represents magnesium, manganese, zinc or cobalt, $\underline{x}$, $\underline{y}$ and $\underline{z}$ represent the mole fractions of M, aluminum and phosphorus, respectively, present as tetrahedral oxides. The fractions are such that they are within a tetragonal compositional area defined by points ABC and D of FIG. 1 of the drawings of the patent. This patent, at column 6, describes the use of aluminophosphates as a source of phosphorus (lines 26–28) and as a source of aluminum (lines 38–40), and the use of seed crystals to aid in the crystallization of the desired molecular sieve (lines 59–63). Example 85 depicts the use of MAPO-36 as a seed for making MnAPO-36. The chemical composition of the MnAPO-36 fails to reveal the presence of any magnesium. |
| U.S. Pat. No. 4,440,871 | SAPO molecular sieves are a general class of microporous crystallilne silicoaluminophosphates. The pores have a nominal diameter of greater than about 3 Å. The "essentially empirical composition" is $mR:(Si_xAl_yP_z)O_2$, where $\underline{R}$ represents at least one organic templating agent present in the intracrystalline pore system; $\underline{m}$ has a typical value of from 0 to 0.3 and represents the moles of $\underline{R}$ present per mole of $(Si_xAl_yP_z)O_2$; $\underline{x}$, $\underline{y}$ and $\underline{z}$ represent the mole fractions of silicon, aluminum and phosphorus, respectively present as tetrahedral oxides. The fractions are such that they are within a pentagonal compositional area defined by points A, B, C, D and E of the ternary diagram of FIG. 1 and preferably within the pentagonal compositional area defined by points a, b, c, d and e of FIG. 2, of the drawings of the patent. The SAPO molecular sieves have a characteristic x-ray powder diffraction pattern which contains at least the d-spacings set forth in any one of Tables I, III, V, VII IX, XI, XIII, XV, XVII, XIX, XXI, XXIII or XXV of the patent. Further, the as-synthesized crystalline silicoaluminophosphates of the patent may be calcined at a temperature sufficiently high to remove at least some of any organic templating agent present in the intracrystalline pore system as a result of such synthesis. The silicoaluminophosphates are generally referred to therein as "SAPO", as a class, or as "SAPO-n" wherein "n" is an integer denoting a particular SAPO as its preparation is reported in the patent. The U.S. patent speaks at column 8, lines 12–16 of employing seed crystals to generate SAPO species. That technique is described in examples 22, 51 and 53. |
| U.S. Ser. No. 600,312 filed April 13, 1984, commonly assigned, EPC | ELAPSO molecular sieves have the units $ELO_2^n$, $AlO_2^-$, $PO_2^+$, $SiO_2$ in the framework structure and have an empirical chemical composition on an anhydrous basis expressed by the formula: $mR:(EL_wAl_xP_ySi_z)O_2$ |

TABLE A-continued

| | |
|---|---|
| Public. 0 159 624, published October 30, 1985 | where "EL" represents at least one element present as a framework oxide unit "$ELO_2{}^n$" with charge "n" where "n" may be $-3, -2, -1, 0$ or $+1$; "R" represents at least one organic templating agent present on the intracrystalline pore system; "m" represents the molar amount of "R" present per mole of $(EL_wAl_xP_ySi_z)O_2$ and has a value from zero to about 0.3; and "w", "x", "y" and "z" represent the mole fractions of $ELO_2{}^n$, $AlO_2{}^-$, $PO_2{}^+$, $SiO_2$, respectively, presnt as framework oxide units. "EL" is characterized as an element having (a) a mean "T—O" distance in tetrahedral oxide structures between about 1.51 Å and about 2.06 Å, (b) a cation electronegativity between about 125 kcal/g-atom to about 310 kcal/gm-atom and (c) a capability of forming stable M—O—P, M—O—Al or M—O—M bonds in crystalline three dimensional oxide structures having a "m—O" bond dissociation energy greater than about 59 kcal/g-atom at 298° K. "w", "x", "y" and "z" represent the mole fractions of "EL", aluminum, phosphorus and silicon, respectively, present as framework oxides. The mole fractions are within the limiting compositional values or points as follows: |

| | Mole Fraction | | |
|---|---|---|---|
| Point | x | y | (z + w) |
| A | 0.60 | 0.39–(0.01 p) | 0.01(p + 1) |
| B | 0.39–(0.01 p) | 0.60 | 0.01(P + 1) |
| C | 0.01 | 0.60 | 0.39 |
| D | 0.01 | 0.01 | 0.98 |
| E | 0.60 | 0.01 | 0.39 | where "p" is an integer corresponding to the number of elements which "EL" represents in the $(EL_wAl_xP_ySi_z)O_2$ composition. The "EL" of the "ELAPSO" molecular sieves may be defined as representing at least one element capable of forming a framework tetrahedral oxide and is preferably selected from the group consisting of arsenic, beryllium, boron, chromium, cobalt, gallium, germanium, iron, lithium, magnesium, manganese, titanium and zinc and "w", "x", "y" and "z" represent the mole fractions of "EL", aluminum, phosphorus and silicon, respectively, present at tetrahedral oxides in which the mole fractions are within the limiting compositional values or points as follows:

| | Mole Fraction | | |
|---|---|---|---|
| Point | x | y | (z + w) |
| a | 0.60 | 0.39–(0.01 p) | 0.01(p + 1) |
| b | 0.39–(0.01 p) | 0.60 | 0.01(p + 1) |
| c | 0.10 | 0.55 | 0.35 |
| d | 0.55 | 0.10 | 0.35 |

| | |
|---|---|
| | where "p" is as above defined. The EP publication at page 16 discloses the use of crystalline and amorphous aluminophosphate as a source of phosphorus and aluminum and at page 17 describes seeding the reaction mixture. Examples 11A, 12A, 93A–103A, 5B, 6B, 55B, 58B, 59B, 50D–56D, 59D–62D and 12F–15F depict the use of seed crystals. |
| U.S. Pat. No. 4,500,651, patented Feb. 19, 1985 | TAPO molecular sieves comprise three-dimensional microporous crystalline framework structures of $[TiO_2]$, $[AlO_2]$ and $[PO_2]$ tetrahedral units which have a unit empirical formula on an anhydrous basis of: $mR:(Ti_xAl_yP_z)O_2$ (1) wherein "R" represents at least one organic templating agent present in the intracrystalline pore system; "m" represents the moles of "R" present per mole of $(Ti_xAl_yP_z)O_2$ and has a value of from zero to 5.0, the maximum value in each case depending upon the molecular dimensions of the templating agent and the available void volume of the pore system of the particular titanium molecular sieve; "x", "y" |

TABLE A-continued and "z" represent the mole fractions of titanium, aluminum and phosphorus, respectively, present as tetrahedral oxides, representing the following values for "x", "y" and "z":

| Point | Mole Fraction | | |
|---|---|---|---|
| | x | y | (z + w) |
| A | 0.001 | 0.45 | 0.549 |
| B | 0.88 | 0.01 | 0.11 |
| C | 0.98 | 0.01 | 0.01 |
| D | 029 | 0.70 | 0.01 |
| E | 0.0001 | 0.70 | 0.299 |

The parameters "x", "y" and "z" are preferably within the following values for "x", "y" and "z":

| Point | Mole Fraction | | |
|---|---|---|---|
| | x | y | (z + w) |
| a | 0.002 | 0.499 | 0.499 |
| b | 0.20 | 0.40 | 0.40 |
| c | 0.20 | 0.50 | 0.30 |
| d | 0.10 | 0.60 | 0.30 |
| e | 0.002 | 0.60 | 0.398 |

The TAPO molecular sieves are generally further characterized by an intracrystalline adsorption capacity for water at 4.6 torr and about 24° C., of about 3.0 weight percent. The adsorption of water has been observed to be completely reversible while retaining the same essential framework topology in both the hydrated and dehydrated state.

The U. S. patent at column 8, lines 65–68, and column 9, lines 15–18, discusses the use of crytalline amorphous aluminophosphate as a source of phosphorus and aluminum. At column 6, lines 1–5, seeding is described as facilitating the crystallization procedure. Comparative example 44 describes a composition of amorphous $TiO_2$ and 95 wt. % $AlPO_4$18 without an indiation of how the composition was prepared.

U.S. Ser. No. 600,179, filed Apr. 13, 1984, EPC Publication 0 161 488, published Nov. 21, 1985

The TiAPSO molecular sieves have three-dimensional microporous framework structures of $TiO_2$, $AlO_2^-$, $PO_2^+$ and $SiO_2$ tetrahedral oxide units having an empirical chemical composition on an anhydrous basis expressed by the formula:

$mR:(Ti_wAl_xP_ySi_z)O_2$ wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined in respect to the ternary diagram of FIG. 1 of the applications as being within the following limiting compositional values or points:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d of the ternary diagram of FIG. 2 of the applications, said points a, b, c and d representing the following values for "w", "x", "y" and "z":

| Point | Mole Fraction | | |
|---|---|---|---|
| | x | y | (z + w) |
| a | 0.55 | 0.43 | 0.02 |

TABLE A-continued

|   |      |      |      |
|---|------|------|------|
| b | 0.43 | 0.55 | 0.02 |
| c | 0.10 | 0.55 | 0.35 |
| d | 0.55 | 0.10 | 0.35 |

| | |
|---|---|
| | The publication, at page 13, describes the use of crystalline or amorphous aluminophosphate as a source of phosphorus and aluminum and, at page 14, points out that seeding the reaction mixture facilitates the crystallization procedure. |
| U.S. Pat. No. 4,554,143, patented Nov. 19,1985 | Ferroaluminophosphates (FAPO's) are disclosed in U.S. Pat. No. 4,554,143, incorporated herein by reference, and have a three-dimensional microporous crystal framework structure of $AlO_2$, $FeO_2$ and $PO_2$ tetrahedral units and have an essential empirical chemical composition, on an anhydrous basis, of: $mR:(Fe_xAl_yP_z)O_2$ wherein "R" represents at least one organic templating agent present in the intracrystalline pore system; "m" represents the moles of "R" present per mole of $(Fe_xAl_yP_z)O_2$ and has a value of from zero to 0.3, the maximum value in each case depending upon the molecular dimensions of the templating agent and the available void volume of the pore system of the particular ferroaluminophosphate involved; "x", "y" and "z" represent the mole fractions of iron, aluminum and phosphorus, respectively, present as tetrahedral oxides, representing the following values for "x", "y" and "z": |

|       | Mole Fraction | | |
|-------|------|------|---------|
| Point | x    | y    | (z + w) |
| A     | 0.01 | 0.60 | 0.39    |
| B     | 0.01 | 0.39 | 0.60    |
| C     | 0.35 | 0.05 | 0.60    |
| D     | 0.35 | 0.60 | 0.05    |

When synthesized the minimum value of "m" in the formula above is 0.02. In a preferred subclass of the ferroaluminophosphates the values of "x", "y" and "z" in the formula above are representing the following values of "x", "y" and "z":

|       | Mole Fraction | | |
|-------|------|------|---------|
| Point | x    | y    | (z + w) |
| a     | 0.01 | 0.52 | 0.47    |
| b     | 0.01 | 0.39 | 0.60    |
| c     | 0.25 | 0.15 | 0.60    |
| d     | 0.25 | 0.40 | 0.35    |

| | |
|---|---|
| | The iron of the $FeO_2$ structural units can be in either the ferric or ferrous valence state, depending largely upon the source of the iron in the synthesis gel. Thus, a $FeO_2$ tetrahedron in the structure can have a net charge of either $-1$ or $-2$. The patent indicates at column 5, lines 43–45 and 54–56, that crystalline amorphous aluminophosphate may be used as a source of phosphorus and aluminum and at column 6, lines 1–5, describes seeding of the reaction mixture as facilitating the crystallization procedure. |
| U.S. Application S.N. 600,173, filed April 13, 1984, EPC Publication 0 161 491, published Nov. 21, 1985 | The FeAPSO molecular sieves have a three-dimensional microporous crystal framework structures of $FeO_2^{-2}$ (and/or $FeO_2$), $AlO_2$, $PO_2$ and $SiO_2$ tetrahedral oxide units and having a unit empirical formula, on an anhydrous basis, of: $mR:(Fe_wAl_xP_ySi_z)O_2$ (1) wherein "R" represents at least one organic templating agent present in the intracrystalline pore system; "m" represents the moles of "R" present per mole of $(Fe_wAl_xP_ySi_z)O_2$ and has a value of from zero to about 0.3; the maximum value of "m" in each case depends upon the molecular dimensions of the templating agent and the |

TABLE A-continued available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The EP publication, at page 12, describes the use of seeding the reaction mixture to facilitate the crystallization procedure. At page 18, the publication describes the use of crystalline amorphous aluminophosphates as a source of phosphorus and aluminum in making the molecular sieve.

U.S. Ser. No. 600,170, EPC Publication 0 158 975, published Oct. 23, 1985

The ZnAPSO molecular sieves of U.S. Ser. No. 600,170, filed April 13, 1984 comprise framework structures of $ZnO_2^{-2}$, $AlO_2^{-}$, $PO_2^{+}$ and $SiO_2$ tetrahedral units having an empirical chemical composition on an anhydrous basis expressed by the formula:

$mR:(Zn_wAl_xP_ySi_z)O_2$ wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55* | 0.10 | 0.35 |

This publication at page 13 discloses that crystalline or amorphous aluminophosphate may be used as a source of phosphorus or aluminum and at page 14 indicates that seeding of the reaction mixture with said crystals facilitates the crystallization procedure. Examples 12-15 are stated to employ the seeding procedure.

U.S. Application Ser. No. 600,180,

The MgAPSO molecular sieves have three-dimensional microporous framework

TABLE A-continued

| | |
|---|---|
| filed April 13, 1984, EPC Publication 0 158 348, published Oct. 16, 1985 | structures of $MgO_2^{-2}$, $AlO_2^-$, $PO_2^+$ and $SiO_2$ tetrahedral oxide units and have an empirical chemical composition on an anhydrous basis expressed by the formula: $mR:(Mg_wAl_xP_ySi_z)O_2$ wherein "R" represents at least one organic templating agent present in the intracrystalline pore system; "m" represents the molar amount of "R" present per mole of $(Mg_wAl_xP_ySi_z)O_2$ and has a value from zero to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows: |

| | Mole Fraction | | |
|---|---|---|---|
| Point | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

| | |
|---|---|
| | This publication depicts seeding to generate product at page 14 and in examples 5, 6, 55, 58 and 59. |
| U.S. Application Ser. No. 600,175, filed April 4, 1984, EPC Publication 0 161 490, published Nov. 11, 1985 | The MnAPSO molecular sieves of U.S. Ser. No. 600,175, filed April 13, 1984 have a framework structure of $MnO_2^2$, $AlO_2$, $PO_2$, and $SiO_2$ tetrahedral units having an empirical chemical composition on an anhydrous basis expressed by the formula: $mR:(Mn_wAl_xP_ySi_z)O_2$ wherein "R" represents at least one organic templating agent present in the intracrystalline pore system; "m" represents the molar mount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows: |

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w., x, y and z may be as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The publication at page 13 describes the use of crystal or amorphous aluminophosphate as a source of phosphorus or aluminum, and at page

TABLE A-continued

| | |
|---|---|
| | 14 characterizes the use of said crystals to facilitate the crystallization procedure. Examples 54–56 and 59–62 state said crystals were used in the manufacture of the MnAPSO products. |
| U.S. Application Ser. No. 600,174, filed April 13, 1984, EPC Publication 0 161 489, published Nov. 21, 1985 | The CoAPSO molecular sieves of U.S. Ser. No. 600,174, filed April 13, 1984 have three-dimensional microporous framework structures of $CoO_2^2$, $AlO_2$, $PO_2$ and $SiO_2$ tetrahedral units and have an empirical chemical composition on an anhydrous basis expressed by the formula: $mR:(Co_wAl_xP_ySi_z)O_2$ wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represents the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows: |

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

| | |
|---|---|
| | The EP publication at page 13 depicts the use of crystalline amorphous aluminophosphate as a source of phosphorus and aluminum and at page 14 states that seeding the reaction mixture facilitates the crystallization procedure. Examples 11, 12, 13, 93 and 97–103 depict the use of seed crystals. |
| U.S. 599,771 599,776 599,807, 599,809, 599,811 599,812 599,813 600,166 600,171 each filed April 13, 1984, EPC Publication 0 158 976, published Oct. 23, 1985 | MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,028. Members of this novel class of compositons have a three-dimensional microporous crystal framework structure of $MO_2^2$, $AlO_2$ and $PO_2$ tetrahedral units and have the essentially empirical chemical composition, on an anhydrous basis, of: $mR:(M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y" and "z" represent the mole fractions of the metal "M", (i.e., magnesium, manganese, zinc and cobalt), aluminum and phosphorus, respectively, present as tetrahedral oxides, said mole fractions being such that they are representing the |

TABLE A-continued following values for "x", "y" and "z":

| Point | Mole Fraction | | |
|---|---|---|---|
| | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are repesenting the following values for "x", "y" and "z":

| Point | Mole Fraction | | |
|---|---|---|---|
| | x | y | (z + w) |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The as-synthesized compositions are capable of withstanding 350° C. calcination in air for extended periods, i.e., at least 2 hours, without becoming amorphous.
The EP publication at pages 14 and 15 depicts the use of crystalline and amorphous aluminophosphate as a source of phosphorus and aluminum and at page 15 states that seeding the reaction mixture facilitates the crystallization procedure. Example 8 discloses seeding of crystals.

EPC Applic. 85104386.9, filed April 11, 1985 (EPC Publication No. 0158976, published October 13, 1985) and EPC Applic. 85104388.5, filed April 11, 1985 (EPC Publication No. 158348, published October 16, 1985)

"ELAPO" molecular sieves are a class of crystalline molecular sieves in which at least on element capable of forming a three-dimensional miroporous framework form crystal framework structures of $AlO_2$, $Po_2$ and $MO_2$ tetrahedral oxide units wherein "$MO_2$" represents at least one different element (other than Al or P) present as tetrahedral oxide units "$MO_2$" with charge "n" where "n" may be $-3$, $-2$, $-1$, 0 or $+1$. The members of this novel class of molecular sieve compositions have crystal framework structures of $AlO_2$, $PO_2$ and $MO_2$ tetrahedral units and have an empirical chemical composition on an anhydrous basis expressed by the formula: $mR:(M_xAl_yP_z)O_2$ wherein "R" represents at least one organic templating agent present in the intracrystalline pore system; "m" represents the molar amount of "R" present per mole of $(M_xAl_yP_z)O_2$; "M" represents at least one element capable of forming framework tetrahedral oxides; and "x", "y" and "z" represent the mole fractions of "M", aluminum and phosphorus, respectively, present as tetrahedral oxides. "M" is at least one different elements ($M_1$) such that the moleclar sieves contain at least one framework tetrahedral units in addition to $AlO_2$ and $PO_2$. "M" is at least one element selected from the group consisting of arsenic, beryllium, boron, chromium, gallium, germanium and lithium, and when "M" denotes two elements the second element may be one of the aforementioned and/or is at least one element elected from the group consisting of cobalt, iron, magnesium, manganese, titanium and zinc.
The ELAPO molecular sieves are generally referred to herein by the acronym or "ELAPO" to designate element(s) "M" in a framework of $AlO_2$, $PO_2$ and $MO_2$ tetrahedral oxide units. Actual class members will be identified by replacing the "EL" of the acronym with the elements present as $MO_2$ tetrahedral units.
When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and

TABLE A-continued when two or more elements are present, the second and further elements may be selected from the first group of elements and/or the second group of elements, as above discussed.

The ELAPO molecular sieves have crystalline three-dimensional microporous framework structures of $AlO_2$, $PO_2$ and $MO_2$ tetrahedral units and have an empirical chemical composition on an anhydrous basis expressed by the formula:

$mR:(M_xAl_yP_z)O_2$;

wherein "R" represents at least one organic templating agent present in the intracrysralline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc.

The relative amounts of element(s) "M", aluminum and phosphorus are expressed by the empirical chemical formula (anhydrous):

$mR:(M_xAl_yP_z)O_2$ where "x", "y" and "z" represent the mole fractions of said "M", aluminum and phosphorus. The individual mole fractions of each "M" (of when M denotes two or more elements, $M_1$, $M_2$, $M_3$, etc.) may be represented by "$x_1$", "$x_2$", "$x_3$", etc. wherein "$x_1$", "$x_2$", and "$x_3$", and etc. represent the individual mole fractions of elements $M_1$, $M_2$, $M_3$, and etc. for "M" as above defined. The values of "$x_1$", "$x_2$", "$x_3$", etc. are as defined for "x" hereinafter, where "$x_1$" + "$x_2$" + "$x_3$" ... = "x" and where $x_1$, $x_2$, $x_3$, etc. are each at least 0.01.

The ELAPO molecular sieves have crystalline three-dimensional microporous framework structures of $MO_2$, $AlO_2$ and $PO_2$ tetrahedral units having an empirical chemical composition on an anhydrous basis expressed by the formula:

$mR:(M_xAl_yP_z)O_2$ wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; said mole fractions "x", "y" and "z" being generally defined as within the following values for "x", "y", and "z":

| Point | Mole Fraction | | |
|---|---|---|---|
| | x | y | (z + w) |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred sub-class of the ELAPOs of this invention, the values of "x", "y" and "z" in the formula above are within the following values for "x", "y" and "z":

| Point | Mole Fraction | | |
|---|---|---|---|
| | x | y | (z + w) |
| a | 0.02 | 0.60 | 0.39 |
| b | 0.02 | 0.38 | 0.60 |
| c | 0.39 | 0.01 | 0.60 |

TABLE A-continued

| | | | |
|---|---|---|---|
| d | 0.60 | 0.01 | 0.39 |
| e | 0.60 | 0.39 | 0.01 |
| f | 0.39 | 0.60 | 0.01 |

| | |
|---|---|
| U.S. Pat. No. 4,310,440 | ALPO's are the basic and simplest of the crystalline aluminophosphates. They each having a framework structure whose chemical composition expressed in terms of mole ratios of oxides is: $Al_2O_3:1.0 \pm 0.2P_2O_5$: each of said framework structures being microporous in which the pores are uniform and have nominal diameters within the range of about 3 to about 10 Å, an intracrystalline adsorption capacity for water at 4.6 torr and 24° C. of at least 3.5 weight percent, the absorption and desorption of water being completely reversible while retaining the same essential framework topology in both the hydrated and dehydrated state. |
| U.S. Pat. Applications 600,168, 600,181, 600,182, 600,183, European Patent Publ. 0 158 350, publ. Oct. 16, 1985 | SENAPSO are quinary and senary molecular sieves that have framework structures of at least two elements haing tetrahedral oxide units "$MO_2{}^n$" and having $AlO_2{}^-$, $PO_2{}^+$ $SiO_2$ tetrahedral oxide units, where "n" is $-3$, $-2$, $-1$, 0 or $+1$, and have an empirical chemical composition on an anhydrous basis expressed by the formula: $mR:(M_wAl_xP_ySi_z)O_2$ wherein "R" represents at least one organic templating agent present in the intracrystalline pore system; "m" represents the molar amount of "R" present per mole of $(M_wAl_xP_ySi_z)O_2$ and has a value of from 0 to about 0.3; "M" represents at least two elements selected from the group consisting of arsenic, beryllium, boron, chromium, cobalt, gallium, germanium, iron, lithium, magnesium, manganese, titanium, vanadium, and zinc; "n" is as above defined; and "w", "x", "y" and "z" represent the mole fractions of elements "M", aluminium, phosphorus and silicon, respectively, present as tetrahedral oxides, each having a value of at least 0,01. The publication, at pages 14–15, generally describes seeding reaction mixtures to form the desired product. |

Zeolitic molecular sieves may be represented by the general formula:

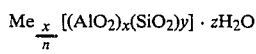

$$Me_{\frac{x}{n}}[(AlO_2)_x(SiO_2)_y] \cdot zH_2O$$

where Me is a metal cation, x/n is the number of exchangeable metal cations of valence n, x is also the number of aluminum ions combined in the form of aluminate, y is the number of silicon atoms and z is the number of water molecules, removal of which produces the characteristic pore or channel system. The ratio z/x is a number from 1 to 5, usually from 1 to 2.

Typical of the zeolitic molecular sieves are chabazite, faujasite levynite, Linde Type A, gismondine, erionite, sodalite, Linde Type X and Y, analcime, gmelinite, harmotome, levynite, mordenite, epistilbite, heulandite, stilbite, edingtonite, mesolite, natrolite, scolecite, thomsonite, brewsterite, laumontite, phillipsite, the ZSM's (e.g., ZSM-5[2], ZSM-20[3], ZSM-12[4], ZSM-34[5], etc.) and Beta[6] and the like. Typical of suitable zeolitic molecular sieves employable in the practice of this invention are the following:

Zeolites-A, AgX, AgY, AlHY, alkylammonium X and Y, BaX, BaY, BeY, Ca-A, Ca-near faujasite, Ca-HX, CA-X, CA-Y, CdX, CdY, CeY, CoA, CoX, CoY, CrY, CsL, CsX, CsY, Cu-X, Cu-Y, Cu-diethylammonium Y, Cu-ethylammonium Y, Fe-X, Fe-Y, group IAX, group IAY, Group IIAY, HY, KL, KX, KY, L, La-X, La-Y, LiA, LiX, LiY, LZ-10, LZ-210, MgHY, MgNa, MgNH4Y, MgX, MgY, MnX, MnY, Na-A, Na-near faujasite, Na-L, Na-X, Na-Y, NH4L, NH4X, NH4Y, Ni-A, Ni-X, Ni-Y, omega, PdY, phosphate, Pt, rare earth X, rare earth Y, RbX, RhY, SrX, SrY, steam stabilized or ultra-stable Y, tetramethylammonium Y, TIX, triethylammonium Y, X, Y, Y-82, ZK-5, Zn-mordenite, Zn-X, An-Y, Zeolon, the ZSM's, supra, and the like. Other zeolitic CMSCs useful in the present invention include boron-treated aluminosilicates, such as disclosed in U.S. Pat. No. 4,613,720. Other NZMSs include the silica molecular sieves, such as silicalite as depicted in U.S. Pat. No. 4,061,724.

[2] See the U.S. Pat. No. 3,702,886.
[3] See U.S. Pat. No. 3,972,983.
[4] See U.S. Pat. No. 3,832,449.
[5] See U.S. Pat. No. 4,079,095.
[6] See U.S. Pat. No. 3,308,069 and U.S. Pat. No. RE. 28,341.

The average diameter of the pores of the presently useful step (b) CMSCs is preferably in the range of about 3 angstroms to about 15 angstroms as determined by measurements described in "Zeolite Molecular Sieves" by Donald W. Breck, published by John Wiley & Sons, New York, 1974. This average diameter is referred to as the average effective diameter. The step (b) MCSCs preferably has pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the CMSC and adsorption of the adsorbate is over three percent by weight of the adsorbate based on the weight of the CMSC. Certain of the CMCs useful in the present invention have pores with an average effective diameter in the range of about 3 angstroms to about 5 angstroms.

The presently useful step (b) catalysts may be incorporated into solid particles in which the catalyst is present in an amount effective to promote the desired conversion to olefins. In one embodiment, the solid particles comprise a catalytically effective amount of the catalyst and at least one of a filler material and a binder material to provide a desired property or properties, e.g., desired catalyst dilution, mechanical strength and the like, to the solid particles. Such filler and binder materials, i.e, matrix materials, are to some extent porous in nature and may or may not be effective to promote the desired product conversion. If a CMSC is employed in step (b), such matrix materials include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-alumina-zirconias, mixtures of these and the like.

If one or more matrix materials are incuded in the step (b) solid particles, the catalyst preferably comprises about 1% to about 99%, more preferably about 5% to about 90% and still more preferably about 10% to about 80%, by weight of the total solid particles. When the catalyst is a CMSC and is used in a slurry system, e.g., with a suspending liquid other than the feedstock or the product, the catalyst preferably is included in solid particles containing no more than about 75%, more preferably no more than about 35%, by weight of other solid material, e.g., matrix materials. In one embodiment, substantially pure catalyst, i.e., catalyst particles substantially free of matrix materials, are used in the present second or step (b) reaction zone, particularly when such catalyst is a CMSC employed as a catalyst/liquid slurry.

The preparation of solid particles comprising CMSC and matrix materials is conventional and well known in the art and, therefore, need not be discussed in detail here. Certain of such preparation procedures are described in the patents and patent applications previously incorporated by reference herein, as well as in U.S. Pat. No. 3,140,253 and U.S. Pat. No. RE. 27,639. Catalysts which are formed during and/or as part of the methods of manufacturing the solid particles are within the scope of the present invention.

The solid particles including the step (b) catalysts may be of any size functionally suitable in the present invention. In order that the catalyst can be utilized more effectively, the solid particles are preferably small relative to fixed bed solid particles used to promote similar chemical conversions. More preferably, the solid particles have a maximum transverse dimension, e.g., diameter, in the range of about 1 micron to about 500 microns, still more preferably about 25 microns to about 200 microns.

The step (b) catalyst and/or solid particles may be subjected to mechanical size reduction, e.g., grinding, crushing, milling and the like, in order to obtain the desired particle size. However, it is preferred that the solid particles including the catalyst be more smooth, and more preferably also more spherical, relative to solid particles of similar composition obtained by mechanical size reduction. Such particle smoothness and sphericity tends to improve the flow properties and useful life of the catalyst and may also allow increased solids loading in a catalyst/liquid slurry, if desired. One particularly useful processing step to achieve such smoothness and sphericity is to employ spray drying as part of the solid particle manufacturing process to form the solid particles or precursors of the solid particles. An additional advantage of employing such spray drying is that the conditions of such a step can be controlled so that the product solid particles are of a desired particle size or size range. The use of spray drying in such catalyst/solid particle manufacturing is conventional and well known, and therefore need not be discussed in detail here.

The non-zeolitic molecular sieves of NZMSs are particularly useful in the practice of the present invention. Among the NZMSs, the SAPOs are particularly useful. SAPO-17 and SAPO-34, which is described in detail in Example 38 of U.S. Pat. No. 4,440,871, are especially preferred step (a) catalysts. Currently, SAPO-34 is most preferred.

The amount of catalyst or solid particles in the second or step (b) reaction zone, may vary over a wide range depending, for example, on the specific processing application involved. If a catalyst/liquid slurry is employed, relatively high loadings of catalyst/solid particles in the slurry may be appropriate in order to contact the product, e.g., methanol, and catalyst in a space and time effective manner. On the other hand, excessive catalyst/solid particle loadings are to be avoided since reduced desired olefin yield might result. Preferably, the catalyst/solid particles comprise about 0.1% to about 50%, more preferably about 0.2% to about 30%, by weight of the slurry.

If a slurry system is employed, it is preferred to use a suspending liquid in the presently useful slurry which is less reactive than the product or products, e.g., methanol, in the first reaction zone effluent fed to step (b). That is, the suspending liquid is less likely to chemically react, e.g., by itself or with such product or products, olefins product and diluent, at the conditions of step (b). Thus, the rate of chemical conversion or reaction of the suspending liquid is reduced, preferably substantially reduced, relative to such rate for product conversion at the conditions of step (b). More preferably, the suspending liquid is substantialy non-reactive, i.e., does not substantially chemically react or is substantially chemically inert, at the conditions of step (b), particularly with regard to chemical reactions promoted by the presently useful step (b) catalyst. The suspending liquid may degrade or deteriorate, e.g., by oxidation, thermal cracking and the like, over a relatively long period of time at contacting conditions, e.g., elevated temperature. Such degradation or deterioration may result in replacing the suspending liquid, but should not be considered in determining whether the liquid is substantially non-reactive. Preferably, the composition of the suspending liquid is chosen so that the size and/or shape of the liquid's molecules are inconsistent with access to the pores of the catalyst. For example, the molecules of the liquid may be too big to enter the pores of the catalyst.

The suspending liquid may be chosen from a wide variety of compositions provided it functions as described herein. The liquid should be stable, i.e., substantially resistant to deterioration or decomposition at the conditions of step (b) which often include elevated temperatures, for example, in excess of about 300° C. In one embodiment, the molecules of the suspending liquid have a kinetic diameter or diameters of a size to substantially prevent such molecules from entering the pores of the CMSC. The liquid may be inorganic or organic. One or more silicones and the like materials may be used as the suspending liquids. Suitable organic liquids preferably include carbon and hydrogen, and more preferably at least one other element, for example, halogen, nitrogen, oxygen, phosphorus, sulfur and mixtures thereof, with liquids comprising carbon, hydrogen and oxygen-containing molecules being particularly useful. Suspending liquids selected from the group consisting of dibenzyl benzenes, diphenyl ether and mixtures thereof have been found to be especially useful.

The suspending liquid is preferably chosen so that the product or products from the step (b) effluent are more soluble than the desired olefins product in the liquid at the step (b) conditions. The solubility of such first effluent product or products in the suspending liquid facilitates effective step (b) contacting, while the relative insolubility of the desired olefins product in the liquid facilitates separation of the desired olefins product from the step (b) catalyst and reduces the destruction, e.g., further chemical conversion, of the desired olefins product to help preserve the desired product. More preferably, the desired olefins product is substantially insoluble in the suspending liquid at the step (b) conditions.

In one embodiment, the suspending liquid includes at least one component effective to improve at least one property of the step (b) catalyst. In the context of this paragraph, the term "catalyst" refers not only to the catalyst itself, but also to the other components, if any, of the solid particles, e.g., matrix materials, as well. Thus, for example, if the binder material is benefited by a component in the liquid and, as a result, the overall performance of the catalyst is improved, at least one property of the catalyst is improved. Therefore, such beneficiation of other component or components of the solid particles is within the scope of this embodiment of the present invention. The selectivity of the step (b) catalyst to the desired products is one particularly useful property that can be improved by a component of the suspending liquid. In situations where a CMSC is present in solid particles containing one or more matrix materials, the suspending liquid preferably includes at least one component to reduce the undesired catalytic activity of such matrix material or materials. In one particular embodiment, the component in the liquid is a base the molecules of which are substantially prevented, e.g., because of size and/or shape considerations, from entering the pores of the CMSC. Such base acts to inactivate or reduce the undesired catalytic activity of the matrix materials without substantially affecting the desired catalytic activity of the CMSC. The base is preferably selected from the group consisting of pyridine, pyridine derivatives, quinoline, quinoline derivatives and mixtures thereof, particularly when the preferred relatively small effective diameter CMSCs are employed. The amount of such components or components included in the suspending liquid may vary over a wide range, provided that such component is effective to improve at least one property of the catalyst. Such component is preferably present in an amount in the range of about 0.01% to about 20%, more preferably about 0.1% to about 15%, by weight of the liquid in the slurry. Such component may be periodically or continuously added to the suspending liquid to provide the desired effect on a continuing basis.

Step (b) of the present process may be conducted with the catalyst presented in the fluidized state, e.g. as a fluidized bed of solid particles, or as a fixed, moving or ebullating bed of solid particles.

In certain instances, it is preferred that the step (b) contacting conditions be such that the contacting temperature exceed the critical temperature of the first reaction zone effluent product or products, e.g., methanol. In other words, in certain embodiments, such product or products are preferably in the supercritical state at the step (b) contacting conditions.

The olefins product obtained from the step (b) contacting will, of course, depending, for example, on the feedstock, catalyst and conditions employed. In one embodiment, the desired olefins product are preferably light olefins, i.e., olefins which contain 2 to about 6, more preferably 2 to about 4, carbon atoms per molecule. When light olefins are the desired product, such olefins are preferably produced as the major hydrocarbon product, i.e., over 50 mole percent of the hydrocarbon product, in the step (b) reaction zone effluent, is light olefins. If a CMSC is employed, the desired olefin product or products preferably have kinetic diameters which allow such product or products to be removed or escape from the pores of the CMSC.

Olefins production from feedstocks, such as methanol and the like, conventionally occurs in the presence of a diluent, preferably acting to moderate the rate, and possibly also the extent, of such feedstock conversion in step (b), and may further act to aid in temperature control. One advantage of the present invention is that certain components of the step (a) reaction zone effluent, e.g., hydrogen, carbon oxides, water and the like, function as diluent in the step (b) reaction. Thus, these other components in the step (a) effluent provide at least part of the diluent material in step (b).

Additional diluent may be added, as desired, to be present during the step (b) contacting. Such additional diluent may be mixed or combined with the first reaction zone effluent prior to the step (b) contacting or it may be introduced into the second or step (b) reaction zone separately from this effluent. Preferably, the first reaction zone effluent and additional diluent are both substantially continuously fed to the second reaction zone during step (b).

Typical of the additional diluents which may be employed in the first instant process are (in addition to the other components of the first reaction zone effluent) helium, argon, nitrogen, carbon monoxide, carbon dioxide, hydrogen, water, aliphatic hydrocarbons, aromatic hydrocarbons and mixtures thereof. The diluent other than the other components of the first reaction zone effluent, if any, is preferably selected from the group consisting of helium, argon, nitrogen, carbon monoxide, carbon dioxide, hydrogen, water and mixtures thereof, with water, nitrogen and mixtures thereof, in particular water, being more preferred. The amount of diluent employed may vary over a wide range. For example, the amount of diluent may be in an amount in the range of about 0.1% or less to about 99% or more of the moles of product or products, e.g., methanol, fed to the second reaction zone.

Step (b) of the present process often results in the olefins production promoting catalyst losing at least a portion of at least one desirable property, e.g., catalytic property. The catalyst is preferably contacted with regeneration medium to improve the effectiveness of the catalyst to promote the desired conversion. For example, the catalyst may become less effective due to formation of carbonaceous deposits or precursors of such deposits in the pores or other parts of the catalyst and/or solid particles during step (b). In one embodiment, the regeneration medium acts to reduce the average kinetic diameter of molecules present in the pores of the catalyst. Such reduction in the kinetic diameter of these molecules is preferably sufficient to allow the resulting molecules to leave or exit the catalyst pores, thereby providing more pores and/or pore volume for the desired conversion. The step (b) catalyst is preferably regenerated, such as for example, by removing carbonaceous deposit material by oxidation in an oxygen-containing atmosphere. If a catalyst/liquid slurry is employed in step (b) and if the suspending liquid is sufficiently stable, the regeneration medium/catalyst contacting can be conducted while the catalyst is slurried with the suspending liquid.

In one embodiment, the step (b) catalyst includes at least one added component effective to promote the action of the regeneration medium. For example, the catalyst may include at least one metal component effective to promote the oxidation of the carbonaceous deposit material. Of course, such metal component should have no substantial adverse effect on the desired olefins production. Examples of such added components include components of transition metals, such as nickel, cobalt, iron, manganese, copper and the like; the platinum group metals such as platinum, palladium, rhodium and the like; and the rare earth metals such as cerium, lanthanum and the like, and mixtures thereof. If an added metal component is used, it is preferred that this component be present as a minor amount, more preferably more preferably about 1 ppm to about 20% by weight (calculated as elemental metal) of the weight of step (b) catalyst, including the matrix materials, employed.

Alternately to the oxidative catalyst regeneration, a reducing medium can be employed to regenerate the step (b) catalyst. Such reducing medium, preferably selected from the group consisting of hydrogen, carbon monoxide and mixtures thereof, and in particular hydrogen, can, for example, be used to react with molecules, e.g., of carbonaceous deposit material precursor, in the pores of the catalyst to produce molecules of reduced kinetic diameter so that such produced molecules can exit the pores of the catalyst. In one embodiment, the reducing medium is hydrogen and the catalyst includes at least one component, preferably a metal component, effective to promote hydrogenation and/or hydrocracking of molecules present on the catalyst, e.g., in the pores of the catalyst, at the conditions of the reductive regeneration.

Combinations of oxidative and reductive step (b) catalyst regeneration may be employed. For example, the hydrogen and carbon monoxide in the first reaction zone effluent subjected to step (b) may at least partially regenerate the step (b) catalyst, thereby prolonging the useful cycle life before the catalyst is subjected to a more complete oxidative regeneration. Of course, oxidative regeneration and reductive regeneration of the step (b) catalyst may be used, alone, as appropriate, rather than in combination.

The conditions at which step (b) occurs can vary widely depending, for example, on the specific feedstock and catalyst employed, and on the specific olefins product desired. The present process is particularly applicable with step (b) temperatures preferably in the range of about 200° C. to about 600° C., or even about 700° C., more preferably about 350° C. to about 550° C. and still more preferably about 400° to about 500° C., with step (b) pressures preferably below about 1500 psig. The residence time of the first reaction zone effluent in the second reaction zone may be independently selected depending, for example on the specific effluent and catalyst employed, and on the specific olefins product desired.

The olefin-containing effluent from the step (b) (second) reaction zone, is subjected to one or more separation steps to recover an olefin-enriched product. Conventional and well known separation techniques, such as distillation, absorption and the like, may be employed to provide at least one olefin-enriched product, i.e., a product having an increased weight concentration of one or more desired olefins relative to the second reaction zone effluent. This olefins recovery step is operated to achieve the desired degree of olefins recovery.

The second reaction zone effluent also contains hydrogen, at least one carbon oxide and hydrocarbons, e.g., light paraffins, other than the desired olefins.

At least one, and preferably all, of hydrogen, carbon monoxide and carbon dioxide from the second reaction zone effluent is subjected to step (a). This "recycle" feature of the present invention provides for increased ultimate yields of the desired olefins. More preferably, substantially all of at least one, and especially all, of the hydrogen, carbon monoxide and carbon dioxide from the effluent of the second reaction zone is subjected to step (a).

As noted above, the effluent from the second reaction zone includes other hydrocarbons, e.g., paraffins, which are not recovered in the olefin-enriched product or products. Conventionally, these other hydrocarbons, which are the product of non-selective or non-desired reactions in step (b), are disposed of or discarded after the olefin-enriched product or products are recovered and thus, represent a reduction in the overall yield of olefins from methanol.

In one embodiment, the present invention further comprises (e) contacting other hydrocarbons, preferably including paraffins, from the effluent of the second reaction zone in a third reaction zone at conditions effective to chemically react or convert the other hydrocarbons to produce hydrogen, carbon monoxide and/or carbon dioxide in the effluent of the third reaction zone; and (f) subjecting at least one, preferably all, of hydrogen, carbon monoxide and carbon dioxide from the effluent of the third reaction zone to step (a). More preferably substantially all of at least one, especially all, of the hydrogen, carbon monoxide and carbon dioxide from the effluent of the third reaction zone is subjected to step (a). In this embodiment, hydrogen and/or carbon monoxide and/or carbon dioxide from the effluent of the second reaction zone may be subjected to at least a portion of step (e) in order to adjust the molar ratio of hydrogen to carbon monoxide to carbon dioxide, as desired, e.g., to obtain improved olefins yields in the present process.

Step (e) of the present invention preferably involves conventional steam reforming, conventional hydrocarbon gasification, conventional partial oxidation or a combination of two or more of these steps. More preferably, at least a portion of the hydrocarbons, other than the olefins product, from the effluent of the step (b) reaction zone is subjected to steam reforming. Step (e) also preferably involves the waer shift reaction to produce one or more synthesis gas components for use in step (a).

Each of the process steps and reactions noted above can be conducted in a manner which is conventional and well known in the art. Therefore, a detailed description of each of these steps and reactions is not presented here. However, it should be noted that the conditions and catalyst or catalysts employed in step (e) and the amounts of hydrogen and/or carbon oxide from the step (b) effluent which are subjected to at least a portion of step (e) and/or which are recycled directly (without being subjected to any of step (e)) to step (a) can, and preferably are, controlled or adjusted to improve the ultimate yield of olefins from the present process.

In one embodiment of the present invention steps (a) and (b) are, in effect, combined into a single step. That is, the chemical reactions or conversions which take place in the first reaction zone or step (a) and the second reaction zone or step (b) occur in a single reaction zone to produce the desired olefins.

This "single contacting" embodiment of the present invention preferably occurs in the presence of a first catalyst, e.g., a solid first catalyst, effective to promote the chemical reaction of hydrogen and at least one carbon oxide to produce at least one product, preferably methanol, and a second catalyst, e.g., a solid second catalyst, effective to promote the chemical reaction of the product to produce olefins. This single contacting may occur in the presence of a physical admixture of the first and second catalysts. Alternately, both the first and second catalysts may be present in the same composition, e.g., in the same solid particles.

The first catalysts useful in the present invention include certain of those catalysts useful in step (a) noted above. Similarly, the present second catalysts include certain of the step (b) catalysts. Care should be exercised to avoid using first and second catalyst together which have a significant detrimental affect on the other catalyst and/or on the present process.

The first catalyst may be any suitable material effective to promote the production of at least one product, e.g., methanol, methyl acetate, ethanol, ethyl acetate and the like, preferably methanol, at the conditions present in the reaction zone. Beside the catalysts listed previously with respect to step (a), suitable first catalysts include components of metals such as metals from Group IB (of the Periodic Table), in particular copper; Group VIB, in particular molybdenum; Group VIII, in particular cobalt; the Actinium Series, in particular thorium; and the like and mixtures thereof. Such metals are often catalytically effective if present in the form of a compound containing at least one non-metallic component, such as sulfur, oxygen, halogen, phosphorus, nitrogen and mixtures thereof. Metal, sulfur-containing components are particularly useful first catalysts.

The first catalysts are often included in solid particles in association with support materials, e.g., such as one or more of the matrix materials noted previously. The first catalyst can be included in the solid particles using conventional techniques, such as impregnation, precipitation, coprecipitation, ion exchange and the like. Catalyst preparation can be completed using conventional techniques such as washing, drying and calcining. The first catalyst metal may be activated, e.g., by contact or reaction with one or moere non-metallic components or precursors thereof, in order to provide a more effective first catalyst. Such activation procedures can be conducted prior to or after the first catalyst metal is associated with the support. Each of these techniques or procedures is well known in the art of catalyst preparation and activation and, therefore, is not discussed in detail here.

The presently useful second catalysts may be selected from among those catalysts useful in step (b). Preferably, the second catalyst is at least one CMSC, as described above.

In one embodiment, the first catalyst is situated in the pores of the second catalyst, in particular a CMSC. This arrangement provides for effective olefins production. Without wishing to be limited to any theory of operation, it is believed that the reactant molecules, e.g., syn gas components, enter the pores of the second catalyst to react in the presence of the first catalyst to produce the desired product or products, e.g., methanol, which is then almost immediately converted into the desired olefin or olefins.

The conditions in the single reaction zone may represent a compromise between those useful to produce the product from syn gas and those useful to produce olefins. Reaction temperatures in the range of about 350° C. and lower are preferred, with temperatures in the range of about 250° C. to about 350° being more preferred.

The single contacting embodiment of the present invention preferably takes place in the presence of additional diluent, as described above.

The effluent from the single reaction zone is processed in a manner substantially similar to the processing involved with respect to the second effluent, i.e., the effluent from step (b), described above. The hydrocarbons, other than those in the olefins product, and/or at least one of hydrogen, carbon monoxide and carbon dioxide in the effluent of the single reaction zone may be processed in a separate reaction zone or zones in a manner analogous to step (e) described above.

Each of the first, second, third, single and separate reaction znes may include a single reactor vessel or a plurality of reaction vessels in series or in parallel.

DETAILED DESCRIPTION OF THE DRAWINGS

Figure 1:
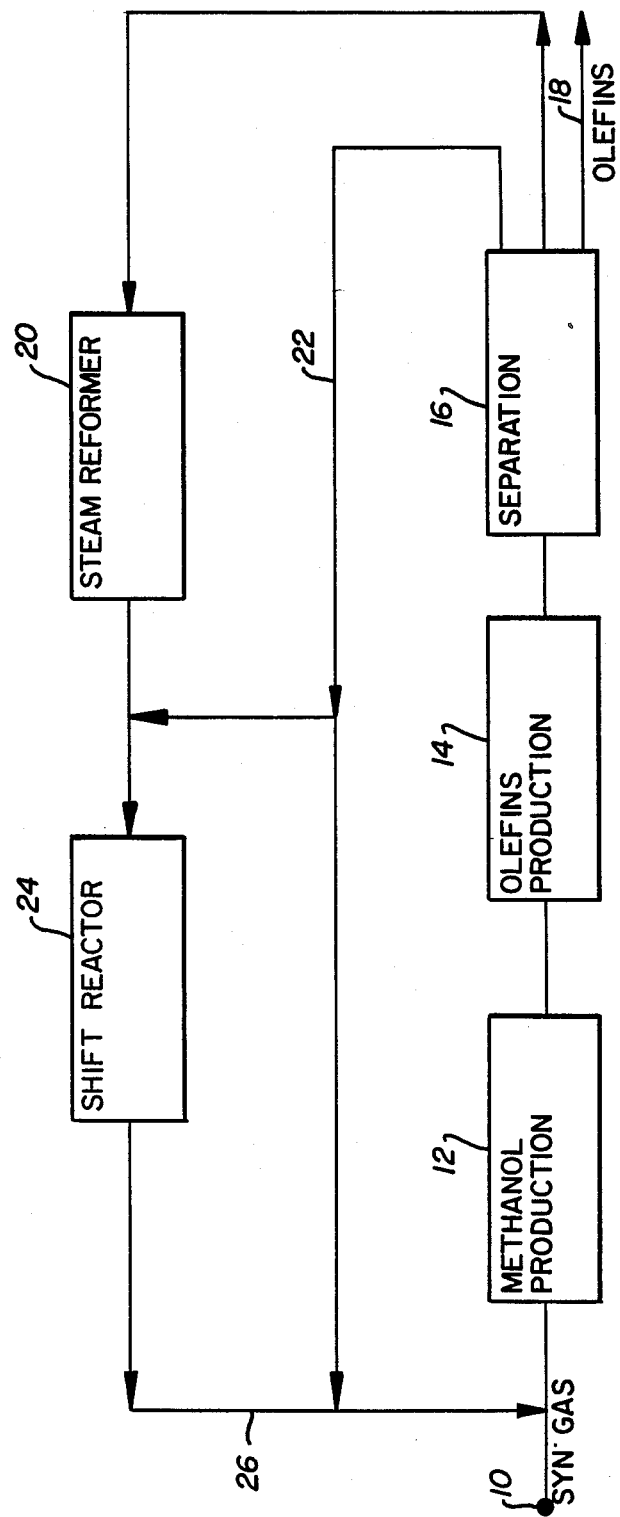
FIG. 1 is a schematic flow diagram of one embodiment of the present invention.

Referring now to FIG. 1, an olefins production process scheme according to the present invention is shown schematically. This process uses synthesis gas from source 10, e.g., a coal gasification plant. Synthesis gas from source 10 is fed to a conventional methanol production reaction system 12 where a major portion of the synthesis gas is converted to oxygenated hydrocarbon products, primarily methanol. The process scheme illustrated in FIG. 1 does not include methanol separation equipment which is conventionally used to recover a specification grade methanol product.

Instead, substantially the entire effluent from reactor system 12 is fed to an olefins production reaction system 14 where the methanol is converted to light olefins primarily. Some paraffins are also produced. Different solid catalysts, as described herein, are employed in each of reaction systems 12 and 14.

The effluent from olefins reaction system 14 is processed in a separation section 16 to recover an olefins-enriched product via line 18. Separation section 16 also yields a paraffin-containing product which is fed to a steam reformer 20, and a product comprising hydrogen, carbon dioxide and carbon monoxide, which is shown leaving separation section 16 in line 22. Separation section 16 may employ any one or a combination of various separation techniques to provide the desired separation. Such separation techniques may include, for example, distillation, absorption, adsorption and the like.

Steam reformer 20 is of conventional design and operation, and converts the paraffins and water to methane and carbon dioxide. This reaction product from steam reformer 20 can be fed directly to methanol conversion reaction system 10, if desired. However, it is preferred that this product, along with at least a portion of the product from line 22 be sent to a conventionally designed and operated water shift reaction system 24. The composition of the material fed to reaction zone 24 is altered or shifted, as desired, to provide for optimum olefins yield. The effluent from reaction system 24 leaves via line 26 and is combined with the remainder, if any, of the product from line 22 and with synthesis gas from source 10. This combined mixture is fed to methanol production reaction system 12 and the operation described above is continuously repeated.

Figure 2:
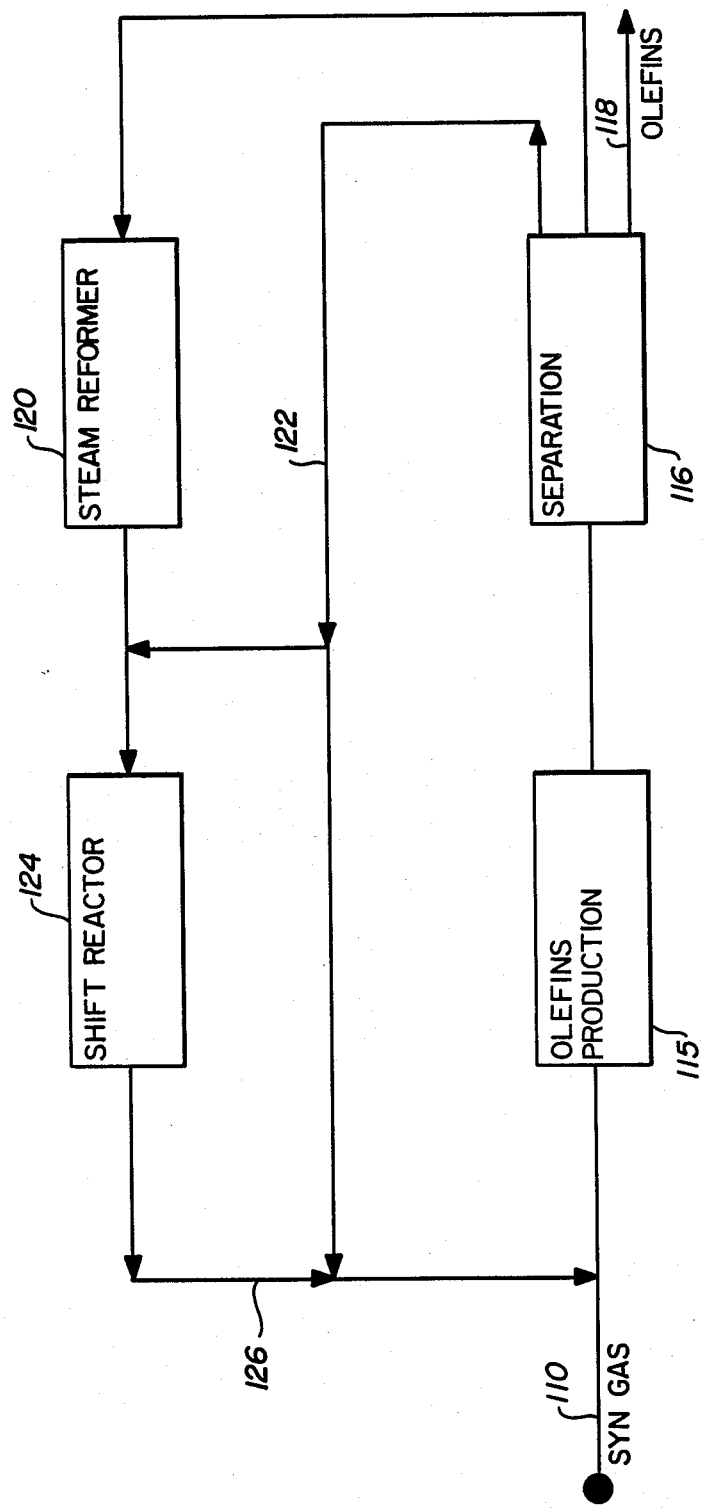
FIG. 2 is a schematic flow diagram of another embodiment of the present invention.

FIG. 2 illustrates a similar operation except that a single reaction system 115 is used to convert synthesis gas from a source 110 into olefins, which are recovered in a separation section 116 as an olefins enriched product from line 118. The solid catalyst in single reaction zone may be a physical admixture of a methanol production catalyst and an olefins production catalyst or it may be a single solid composition, e.g., solid particles, containing both catalysts.

The following non-limiting example is provided to better illustrate the invention.

A commercially sized processing unit is constructed and operated to produce 5000 barrels per day of mixed ethylene and propylene.

The unit involves a conventional synthesis gas production plant which produces a mixture of hydrogen and carbon oxides from coal. This mixture is provided to a methanol production facility which chemically converts hydrogen and carbon oxides to methanol in the presence of a solid catalyst. Since this reaction is equilibrium controlled, the effluent from the reaction section of the facility includes hydrogen, carbon monoxide, carbon dioxide and methanol. This facility is of conventional design except that no separation of the effluent from the reaction section takes place.

This entire effluent is provided to a methanol-to-olefins plant which employs a slurry reaction system. Additional diluent, in the form of water, is added along the methanol-containing material from the methanol production facility. The catalyst employed is SAPO-34. The slurry reaction system is operated so that essentially 100% of the methanol fed to the system is converted.

The effluent from this reaction system is separated to recover an ethylene and propylene enriched product. Paraffins, e.g., $C_6$-paraffins, produced in the slurry reaction system are sent to a conventional steam reformer and a water shift reaction system such that paraffins are converted to hydrogen and carbon oxides which provide a portion of the feedstock to the methanol production facility. Also, the hydrogen and carbon oxides in the effluent from the slurry reaction system are provided to the water shift reaction system. The effluent from this reaction system is sent to the methanol production facility.

This operation is substantially as illustrated in FIG. 1, described above. Alternatively, the functions of the methanol production facility and the methanol-to-olefins plant can be performed in a single reaction system, as illustrated in FIG. 2.

In any event, this integrated processing unit operates effectively to produce the desired quantities of olefins. Substantial capital and operating economies are achieved, for example, because no product separation equipment is present between the methanol production facility and the methanol-to-olefins plant and because the use of paraffins produced acts to increase the ultimate yield of olefins.

While the invention has been described with respect to various specific examples and embodiments, it is to be understood that the present invention is not limited thereto and that it can be variously practiced within the scope of the following claims.

What is claimed is:

1. A process for producing light olefins having less than 5 carbon atoms comprising:
    (a) contacting hydrogen and at least one carbon oxide in a first reaction zone at conditions effective to chemically react said hydrogen and carbon oxide and to produce a product comprising methanol in the effluent of said first reaction zone;
    (b) contacting substantially the entire said first reaction zone effluent in a second reaction zone containing a small pore crystalline microporous three dimensional solid catalyst at conditions effective to promote the conversion of methanol to olefins and to produce said light olefins in the effluent of said reaction zone;
    (c) recovering an olefin-enriched product from said second reaction zone effluent; and
    (d) subjecting at least one of hydrogen and at least one carbon oxide from said second reaction zone effluent to step (a).

2. The process of claim 1 wherein said solid catalyst is selected from the group consisting of layered clays, zeolitic molecular sieves, non-zeolitic molecular sieves and mixtures thereof.

3. The process of claim 1 wherein said solid catalyst is characterized by adsorption of oxygen or xenon or n-hexane and negligible adsorption of isobutane.

4. The process of claim 1 wherein said solid catalyst is present in a fluidized state or in a slurry with a liquid.

5. The process of claim 1 wherein said solid catalyst is present in a slurry with a liquid other than the feedstock to said second reaction zone or the effluent from said first reaction zone.

6. The process of claim 1 wherein said solid catalyst is selected from the group consisting of non-zeolitic molecular sieves and mixtures thereof.

7. The process of claim 1 wherein said solid catalyst is selected from the group consisting of silicoaluminophosphates and mixtures thereof.

8. The process of claim 7 wherein said solid catalyst is selected from the group consisting of SAPO-34, SAPO-17 and mixtures thereof.

9. The process of claim 7 wherein said solid catalyst is SAPO-34.

10. The process of claim 1 wherein both hydrogen and at least one carbon oxide from said effluent of said second reaction zone is subjected to step (a).

11. The process of claim 1 wherein said olefins are selected from the group consisting of ethylene, propylene, butylene and mixtures thereof.

12. A process for producing light olefins having less than 5 carbon atoms comprising:
(1) contacting hydrogen and at least one carbon oxide in a reaction zone containing a first catalyst effective to produce methanol and a second catalyst comprising a small pore crystalline microporous three dimensional solid catalyst at conditions effective to produce said light olefins in the effluent of said reaction zone;
(2) recovering an olefin-enriched product from said effluent of said reaction zone; and
(3) subjecting at least one of hydrogen and at least one carbon oxide from said effluent of said reaction zone to step (1).

13. The process of claim 12 wherein both said first catalyst and said second catalyst are solid.

14. The process of claim 13 wherein step (1) occurs in the presence of a physical admixture of said first catalyst and said second catalyst.

15. The process of claim 13 wherein both said first catalyst and said second catalyst are present in the same solid particles.

16. The process of claim 12 wherein said second catalyst is selected from the group consisting of layered clays, zeolitic molecular sieves and non-zeolitic molecular sieves.

17. The process of claim 12 wherein said second catalyst is characterized by adsorption of oxygen or xenon or n-hexane and negligible adsorption of isobutane.

18. The process of claim 12 wherein said second catalyst is selected from the group consisting of non-zeolitic molecular sieves and mixtures thereof.

19. The process of claim 12 wherein said second catalyst is selected from the group consisting of silicoaluminophosphates and mixtures thereof.

20. The process of claim 19 wherein said second catalyst is selected from the group consisting of SAPO-34, SAPO-17 and mixtures thereof.

21. The process of claim 19 wherein said second catalyst is SAPO-34.

22. The process of claim 15 wherein at least a portion of said first catalyst is located in the pores of said second catalyst.

23. The process of claim 15 wherein a major portion of said first catalyst is located in the pores of said second catalyst.

24. The process of claim 22 wherein said second catalyst is selected from the group consisting of layered clays, zeolitic molecular sieves and non-zeolitic molecular sieves.

25. The process of claim 22 wherein said second catalyst is characterized by adsorption of oxygen or xenon or n-hexane and negligible adsorption of isobutane.

26. The process of claim 22 wherein said second catalyst is selected from the group consisting of non-zeolitic molecular sieves and mixtures thereof.

27. The process of claim 22 wherein said second catalyst is selected from the group consisting of silicoaluminophosphates and mixtures thereof.

28. The process of claim 27 wherein said second catalyst is selected from the group consisting of SAPO-34, SAPO-17 and mixtures thereof.

29. The process of claim 27 wherein said second catalyst is SAPO-34.

30. The process of claim 12 wherein both hydrogen and at least one carbon oxide from said effluent of said second reaction zone is subjected to step (a).

31. The process of claim 12 wherein said effluent from said reaction zone contains paraffins, and said process further comprises (4) contacting paraffins from said effluent of said reaction zone in a separate reaction zone at conditions effective to chemically react said paraffins to produce hydrogen and at least one carbon oxide in the effluent of said separate reaction zone; and (5) subjecting at least at least one of hydrogen and at least one carbon oxide from said effluent of said separate reaction zone to step (4).

32. The process of claim 31 wherein both hydrogen and at least one carbon oxide from said effluent of said separate reaction zone is subjected to step (a).

33. The process of claim 12 wherein said olefins are selected from the group consisting of ethylene, propylene, butylene and mixtures thereof.

34. A process for producing light olefins having less than 5 carbon atoms comprising:
(a) contacting hydrogen and at least one carbon oxide in a first reaction zone at conditions effective to chemically react said hydrogen and carbon oxide and to produce a product comprising methanol in the effluent of said first reaction zone;
(b) contacting substantially the entire said first reaction zone effluent in a second reaction zone containing a small pore crystalline microporous three dimensional slid catalyst at conditions effective to promote the conversion of methanol to olefins and to produce a product comprising said light olefins, paraffins, hydrogen, and at least one carbon oxide in the effluent of said second reaction zone;
(c) separating the effluent from said reaction zone into a product enriched in light olefins, a recycle stream containing paraffins and a recycle stream containing hydrogen and at least one carbon oxide;
(d) converting said product containing paraffins in a third reaction zone at conditions effective to convert the paraffins to a product comprising methane and at least one carbon oxide; and
(e) subjecting at least a portion of the product from said third reaction zone to step (a).

35. The process of claim 34 which further comprises (1) combining at least a portion of said recycle stream containing hydrogen and at least carbon oxide from step (c) with the effluent from said third reaction zone in proportions that provide for improved olefin yield to form a combined stream; (2) passing said combined stream to a water shift reaction system to produce an effluent comprising hydrogen and at least one carbon oxide; and (3) subjecting at least a portion of said effluent from the water shift reaction system along with at least a portion of the uncombined portion of said recycle stream containing hydrogen and at least one carbon oxide from separation step (c) to step (a).

* * * * *